United States Patent
Murphy et al.

(10) Patent No.: US 7,410,482 B2
(45) Date of Patent: Aug. 12, 2008

(54) DETACHABLE ANEURYSM NECK BRIDGE

(75) Inventors: Richard Murphy, Sunnyvale, CA (US); Michael P. Wallace, Fremont, CA (US); Tri Tran, Fremont, CA (US); Kim Nguyen, San Jose, CA (US); Hanh Ho, San Jose, CA (US); My Doan, San Jose, CA (US); Robert M. Abrams, Los Gatos, CA (US); Harold F. Carrison, Pleasanton, CA (US)

(73) Assignee: Boston Scientific-Scimed, Inc., Maple Grove, MN (US)

( * ) Notice: Subject to any disclaimer, the term of this patent is extended or adjusted under 35 U.S.C. 154(b) by 434 days.

(21) Appl. No.: 10/319,379

(22) Filed: Dec. 13, 2002

(65) Prior Publication Data

US 2003/0171739 A1 Sep. 11, 2003

Related U.S. Application Data

(63) Continuation-in-part of application No. 09/548,644, filed on Apr. 13, 2000, now Pat. No. 7,128,736, which is a continuation of application No. 09/148,411, filed on Sep. 4, 1998, now abandoned.

(51) Int. Cl.
*A61B 17/00* (2006.01)

(52) U.S. Cl. .................... 606/1; 606/108; 606/191; 606/213

(58) Field of Classification Search ............... 606/1, 606/108, 191, 213
See application file for complete search history.

(56) References Cited

U.S. PATENT DOCUMENTS

| 3,174,851 A | 3/1965 | Buehler et al. |
| 3,351,463 A | 11/1967 | Rosner et al. |
| 3,753,700 A | 8/1973 | Harrison et al. |
| 4,494,531 A | 1/1985 | Gianturco |
| 4,503,569 A | 3/1985 | Dotter |
| 4,512,338 A | 4/1985 | Balko et al. |
| 4,710,192 A | 12/1987 | Liotta et al. |
| 4,739,768 A | 4/1988 | Engelson |
| 4,820,298 A | 4/1989 | Leveen et al. |
| 4,923,464 A | 5/1990 | DiPisa, Jr. |
| 4,994,069 A | 2/1991 | Ritchart et al. |
| 5,108,407 A | 4/1992 | Geremia et al. |
| 5,122,136 A | 6/1992 | Guglielmi et al. |

(Continued)

FOREIGN PATENT DOCUMENTS

EP 0 820 726 1/1996

(Continued)

*Primary Examiner*—Lee S Cohen
(74) *Attorney, Agent, or Firm*—Vista IP Law Group LLP

(57) ABSTRACT

In one embodiment, a neck bridge for bridging the neck of an aneurysm includes a junction region, a number of radially extending array elements attached to the junction region, and a cover attached to one or both of the junction region and an array element. The array elements are configured to be positioned within the aneurysm after the neck bridge is deployed from a delivery device. In a second embodiment, the neck bridge includes a junction region and a braided or mesh-like structure secured to the junction region. The braided or mesh-like structure is made from an elastic material.

19 Claims, 9 Drawing Sheets

U.S. PATENT DOCUMENTS

| | | |
|---|---|---|
| 5,217,484 A | 6/1993 | Marks |
| 5,226,911 A | 7/1993 | Chee et al. |
| 5,234,437 A | 8/1993 | Sepetka |
| 5,250,071 A | 10/1993 | Palermo |
| 5,261,916 A | 11/1993 | Engelson |
| 5,304,195 A | 4/1994 | Twyford, Jr. et al. |
| 5,312,415 A | 5/1994 | Palermo |
| 5,350,397 A | 9/1994 | Palermo et al. |
| 5,354,295 A | 10/1994 | Guglielmi et al. |
| 5,397,331 A | 3/1995 | Himpens et al. |
| 5,417,708 A | 5/1995 | Hall et al. |
| 5,423,829 A | 6/1995 | Pham et al. |
| 5,496,277 A | 3/1996 | Termin et al. |
| 5,527,338 A | 6/1996 | Purdy |
| 5,562,726 A | 10/1996 | Chuter |
| 5,624,449 A | 4/1997 | Pham et al. |
| 5,669,905 A | 9/1997 | Scheldrup et al. |
| 5,690,671 A | 11/1997 | McGurk et al. |
| 5,718,711 A | 2/1998 | Berenstein et al. |
| 5,725,552 A | 3/1998 | Kotula et al. |
| 5,733,294 A | 3/1998 | Forber et al. |
| 5,743,905 A | 4/1998 | Eder et al. |
| 5,855,578 A | 1/1999 | Guglielmi et al. |
| 5,891,128 A | 4/1999 | Gia et al. |
| 5,891,130 A | 4/1999 | Palermo et al. |
| 5,895,385 A | 4/1999 | Guglielmi et al. |
| 5,916,235 A | 6/1999 | Guglielmi |
| 5,925,037 A | 7/1999 | Guglielmi et al. |
| 5,925,060 A | 7/1999 | Forber |
| 5,925,062 A | 7/1999 | Purdy |
| 5,928,226 A | 7/1999 | Guglielmi et al. |
| 5,928,260 A * | 7/1999 | Chin et al. .................. 606/200 |
| 5,935,148 A | 8/1999 | Villar et al. |
| 5,941,888 A | 8/1999 | Wallace et al. |
| 5,944,714 A | 8/1999 | Guglielmi et al. |
| 5,947,962 A | 9/1999 | Guglielmi et al. |
| 5,947,963 A | 9/1999 | Guglielmi |
| 5,964,797 A | 10/1999 | Ho |
| 5,976,126 A | 11/1999 | Guglielmi |
| 5,984,929 A | 11/1999 | Bashiri et al. |
| 6,010,498 A | 1/2000 | Guglielmi |
| 6,063,070 A | 5/2000 | Eder |
| 6,063,104 A | 5/2000 | Villar et al. |
| 6,066,133 A | 5/2000 | Guglielmi et al. |
| 6,077,260 A | 6/2000 | Wheelock et al. |
| 6,083,220 A | 7/2000 | Guglielmi et al. |
| 6,086,577 A | 7/2000 | Ken et al. |
| 6,156,061 A | 12/2000 | Wallace et al. |
| 6,165,178 A | 12/2000 | Bashiri et al. |
| 6,168,622 B1 | 1/2001 | Mazzocchi |
| 6,193,708 B1 | 2/2001 | Ken et al. |
| 6,331,184 B1 * | 12/2001 | Abrams ...................... 606/200 |
| 6,344,041 B1 | 2/2002 | Kupiecki et al. |
| 6,371,972 B1 | 4/2002 | Wallace et al. |
| 6,375,669 B1 | 4/2002 | Rosenbluth et al. |
| 6,383,171 B1 | 5/2002 | Gifford et al. |
| 6,383,174 B1 | 5/2002 | Eder |
| 6,397,850 B1 | 6/2002 | Scheldrup et al. |
| 6,409,721 B1 | 6/2002 | Wheelock et al. |
| 6,425,893 B1 | 7/2002 | Guglielmi |
| 6,425,914 B1 | 7/2002 | Wallace et al. |
| 6,428,557 B1 | 8/2002 | Hilaire |
| 6,463,317 B1 | 10/2002 | Kucharczyk et al. |
| 6,468,266 B1 | 10/2002 | Bashiri et al. |
| 6,478,773 B1 | 11/2002 | Gandhi et al. |
| 2002/0143349 A1 | 10/2002 | Gifford, III et al. |

FOREIGN PATENT DOCUMENTS

| | | |
|---|---|---|
| WO | WO 97/26938 | 7/1997 |
| WO | WO 97/31672 | 9/1997 |
| WO | WO 99/05977 A | 2/1999 |
| WO | WO 99/07294 | 2/1999 |
| WO | WO 00/13593 | 3/2000 |

* cited by examiner

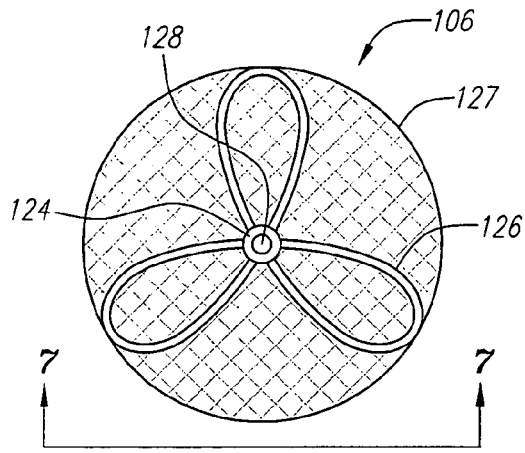 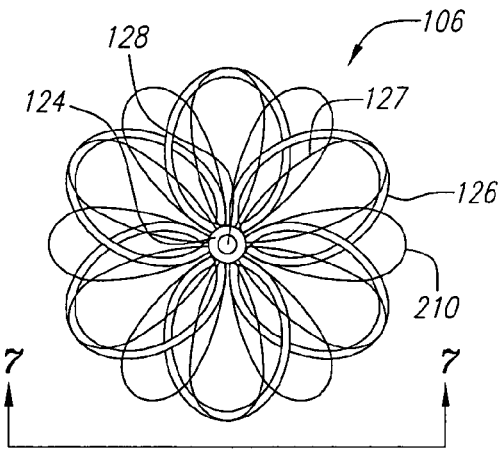
FIG. 5  FIG. 6
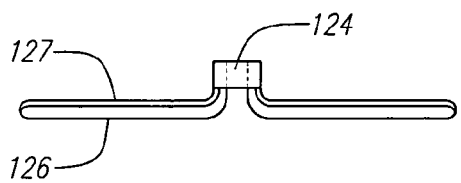 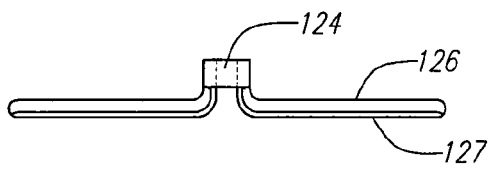
FIG. 7A  FIG. 7B
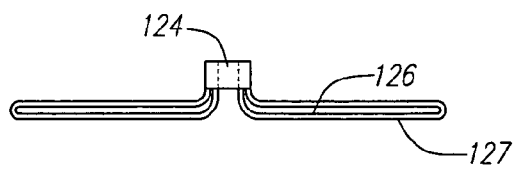
FIG. 7C
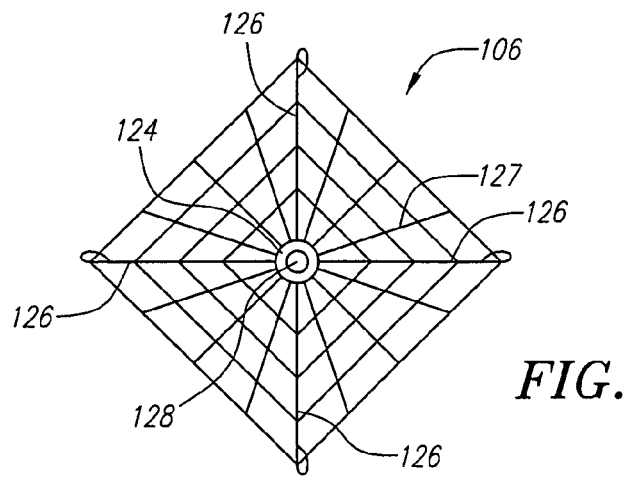
FIG. 8

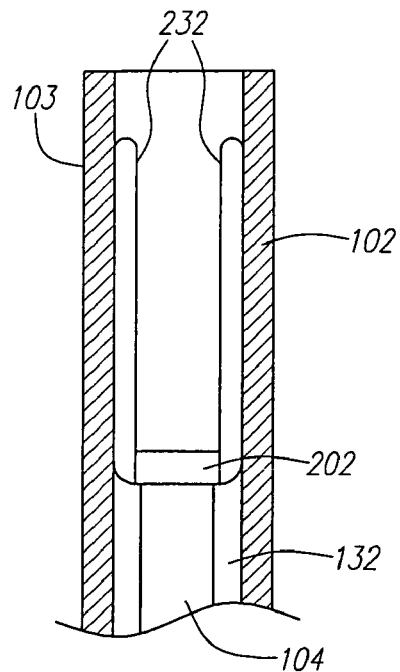
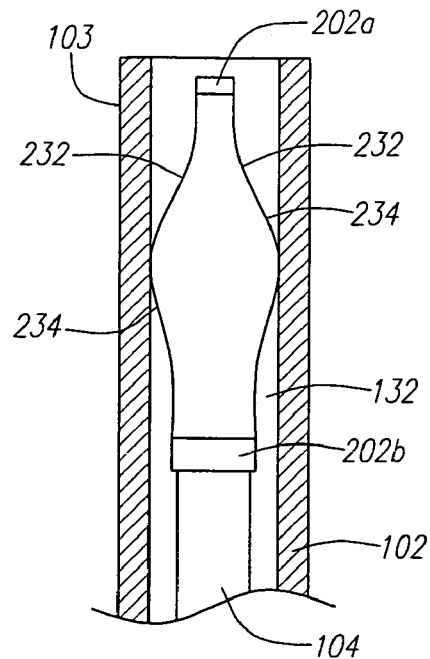
FIG. 14A    FIG. 15A
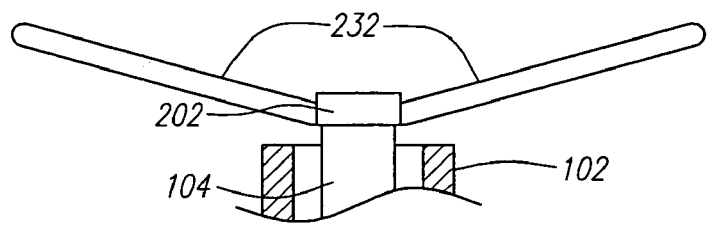
FIG. 14B
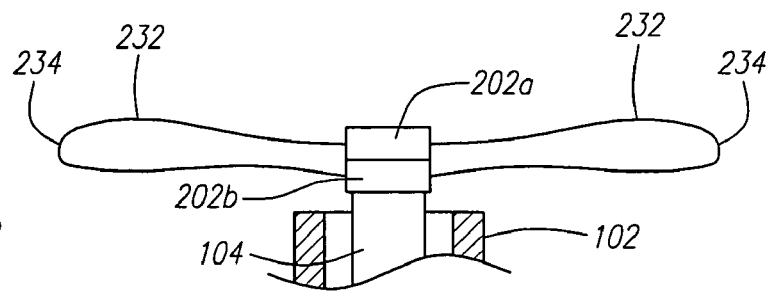
FIG. 15B

DETACHABLE ANEURYSM NECK BRIDGE

RELATED APPLICATION DATA

This application is a continuation-in-part of U.S. patent application Ser. No. 09/548,644 filed Apr. 13, 2000, now U.S. Pat. No. 7,128,736 which is a continuation of U.S. patent application Ser. No. 09/148,411 filed Sep. 4, 1998, now abandoned, the disclosures of which are expressly incorporated by reference herein.

FIELD OF THE INVENTION

The inventions disclosed herein pertain to systems, apparatus, and methods for treating aneurysms, and more specifically, to systems, apparatus, and methods for bridging a neck of an aneurysm.

BACKGROUND

Various implantable medical devices have been developed for treating a number of ailments associated with body lumens. In particular, occlusive devices have been proven useful in filling vascular aneurysms, which are formed due to a weakening in the wall of an artery. Vascular aneurysms are often the site of internal bleeding and stroke. A variety of different embolic agents are known to be, at least arguably, suitable for treatment of vascular aneurysms by filling them to prevent further vessel wall weakening or rupture. Use of these agents are commonly known as "artificial vaso-occlusion."

Over the past few years, advancements in the artificial occlusion of vessels and aneurysms have included the delivery and implantation of metal coils as vaso-occlusive devices. Implantable metal coils that are useful as artificial occlusion devices in vasculature lumens or aneurysms are herein referred to as "vaso-occlusive coils." Vaso-occlusive coils are typically constructed of a wire made of a metal or metal alloy wound into a helix. Such vaso-occlusive coils are typically manufactured to assume a certain shape upon discharge of the device from the distal end of the catheter into a treatment site. A variety of such vaso-occlusive coils are known. For instance, U.S. Pat. No. 4,994,069, issued to Ritchart et al., discloses a flexible, preferably coiled wire for use in small vessel vaso-occlusion. Unlike vaso-occlusive coils used prior to that time, Ritchart et al. discloses using a coil that is relatively soft and is delivered to the site using a pusher within a catheter lumen. Upon discharge from the delivery catheter, the coil may undertake a number of random or pre-determined configurations useful to fill the site.

Known vaso-occlusive coils may be used for filling relatively small vessel sites, e.g., 0.5-6.0 mm in diameter. The coils themselves are described as being between 0.254 and 0.762 mm in diameter. The length of the wire making up the vaso-occlusive coil is typically 15 to 20 times the diameter of the vessel to be occluded. The wire used to make up the coils may be, for instance, 0.051 to 0.152 mm in diameter. Tungsten, platinum, and gold threads or wires are typically preferred. These coils have a variety of benefits, including the fact that they are relatively permanent, they may be easily imaged radiographically, they may be located at a well defined vessel site, and they can be retrieved, if necessary.

In addition to the various types of known space filling mechanisms and geometries of vaso-occlusive coils, other particularized features of coil designs, such as mechanisms for their delivery through catheters and implanting them in a desired occlusion site, are well know in the art. Examples of known vaso-occlusive coils categorized by their delivery mechanisms include pushable coils, mechanically detachable coils, and electrolytically detachable coils.

One example of a "pushable coil" is disclosed in Ritchart et al., discussed above. Pushable coils are commonly provided in a cartridge and are pushed or "plunged" from the cartridge into a lumen of a delivery catheter. A pusher (e.g., a wire or a pressurized fluid) advances the pushable coil through and out of the delivery catheter lumen, into the desired occlusion site.

Mechanically detachable vaso-occlusive coils are typically integrated with a pusher rod and are mechanically detached from the distal end of that pusher after exiting a delivery catheter. Examples of such mechanically detachable vaso-occlusive coils are found in U.S. Pat. No. 5,261,916 to Engelson and U.S. Pat. No. 5,250,071 to Palermo.

Examples of electrolytically detachable vaso-occlusive coils may be found in U.S. Pat. Nos. 5,122,136 and 5,354,295 issued to Guglielmi et al. In these devices, the vaso-occlusive portion of the assembly is attached to a pusher via a small, electrolytically severable joint. The electrolytically severable joint is eroded by the placement of an appropriate voltage on the core wire.

As noted above, aneurysms present a particularly acute medical risk due to the dangers of potential rupture of the thin vascular wall inherent in such aneurysms. Occlusion of aneurysms by use of vaso-occlusive coils without occluding the adjacent artery is a special challenge and is a desirable method of reducing such risk of rupture. Vaso-occlusive devices may be placed in an aneurysm in a manner described in U.S. Pat. No. 4,739,768 issued to Engelson. In particular, a microcatheter is initially steered into or adjacent to the entrance of an aneurysm, typically aided by the use of a steerable guidewire. The wire is then withdrawn from the microcatheter lumen and replaced by one or more vaso-occlusive coils, which are then advanced through and out of the microcatheter, and into the aneurysm.

However, after, or perhaps during delivery of a coil into the aneurysm, there is a risk that a portion of the coil might migrate out of the aneurysm entrance zone and into the feeding vessel. The presence of the coil in that feeding vessel may cause a highly undesirable occlusion there. Also, there is a risk that the blood flow in the vessel and aneurysm may induce movement of the coil farther out of the aneurysm, resulting in a more developed embolus in the feeding vessel.

One type of aneurysm, commonly known as a "wide neck" aneurysm, is known to present particular difficulty in the placement and retention of vaso-occlusive coils, because vaso-occlusive coils lacking substantial secondary shape strength may be difficult to maintain in position within an aneurysm no matter how skillfully they are placed. Wide neck aneurysms are herein referred to as aneurysms of vessel walls having a neck or "entrance zone" from the adjacent vessel, wherein the entrance zone has a diameter that either: (1) is at least 80% of the largest diameter of the aneurysm; or (2) is clinically observed to be too wide effectively to retain commercially available vaso-occlusive coils that are deployed using the techniques discussed above.

Certain techniques have been developed in order to deal with the disadvantages associated with embolic material migration into the parent vessel. One such technique, commonly referred to as flow arrest, involves temporarily occluding the parent vessel proximal of the aneurysm, so that no blood flow occurs through the parent vessel until a thrombotic mass has formed in the sac of the aneurysm. While this technique helps reduce the tendency of the embolic material to migrate out of the aneurysm sac, a thrombotic mass can still dissolve through normal lysis of blood. Also, occluding the parent vessel may not prevent all embolic material migration into the parent vessel. Further, in certain cases, it is highly undesirable to occlude the parent vessel even temporarily. Thus, a flow arrest technique is, at times, not effective or even not available as a treatment option.

Another approach to occlude a wide neck aneurysm is described in U.S. Pat. No. 6,168,622 ("the '622 patent"), which describes a vaso-occlusive device with a secondary shape having a bulbous body portion and an anchor. The bulbous body portion is deployed within the aneurysm while the anchor is set just outside of the aneurysm, covering the aneurysm's neck or entrance zone. As described in the '622 patent, the device may be integrally formed from a tube—clamped at both ends—of braided Nickel-Titanium (NiTi) wires. The bulbous body functions to occlude the aneurysm, while the anchor covers the entrance zone. In some cases, it may still be desirable to deploy vaso-occlusive coils with such a device, but the bulbous body of the vaso-occlusive device may not provide much space within the aneurysm to allow for insertion and deployment of coils.

SUMMARY OF THE INVENTION

In accordance with one aspect of the present invention, a neck bridge for bridging across a neck of an aneurysm comprises a junction region, one or more array elements attached to the junction region, and a cover attached to the junction region. The cover may alternatively be attached to the array elements, or to both the array elements and the junction region. By way of non-limiting examples, the array element may have a shape of a loop, a substantially rectilinear shape, or a curvilinear shape. In preferred embodiments, the array element may be stretched into a delivery shape when positioned within a lumen of a delivery catheter, and assumes an unfolded configuration when unconfined outside the lumen. Suitable materials for construction of the array element include, but are not limited to, elastic and super elastic materials, such as Nitinol.

By way of non-limiting examples, the cover may be a fabric, a woven or non-woven mesh, or other sheeting or planar structure. In one embodiment, the cover may comprise a braided or mesh-like structure that includes a plurality of loops, each loop comprising a fiber having ends secured to the junction region. In preferred embodiments, the cover folds into a low profile structure when positioned within the delivery catheter lumen, and is unfolded by the array elements when the array elements assume an unfolded configuration outside the lumen.

Embodiments of the neck bridge may be detachably coupled to a distal end of a delivery member, a core wire, or similar structure via an electrilytically severable joint or a mechanical joint.

In accordance with another aspect of the present invention, a neck bridge for bridging across a neck of an aneurysm comprises a junction region and a braided (or "mesh-like") structure attached to the junction region. The braided structure is preferably made of an elastic or super-elastic material, and is capable of being stretched into a delivery shape when positioned in a lumen of a delivery catheter. The braided structure assumes an unfolded configuration when unconfined outside the delivery lumen. In one embodiment, the braided structure comprises a plurality of loops, each loop comprising a fiber having ends secured to the junction region. In another embodiment, the junction region includes a first portion and a second portion, and the braided structure comprises a plurality of loops, each loop comprising a fiber having a first end secured to the first portion, and a second end secured to the second portion.

Other embodiments of the neck bridge in accordance with the second aspect of the invention are also described. By way of non-limiting examples, the neck bridge may optionally be detachably coupled to a distal end of a delivery member, a core wire, or similar structures via an electrilytically severable joint or a mechanical joint.

Other aspects, features, and embodiments of the invention are described herein.

BRIEF DESCRIPTION OF THE DRAWINGS

The drawings illustrate the design and utility of preferred embodiments of the present invention, in which similar elements are referred to by common reference numerals. It should be understood that these drawings depict only typical embodiments of the invention and are therefore not to be considered limiting of its scope.

FIG. 5 is a top view of the neck bridge of FIG. 1;

FIG. 6 is a top view of a variation of the neck bridge, particularly showing a cover having a plurality of loops;

FIGS. 7A-7C are side views of further variations of the neck bridge;

FIG. 8 is a top view of a still further variation of the neck bridge, particularly showing the array elements having substantially rectilinear shapes;

FIGS. 14A and 14B show a delivery shape and an unfolded configuration, respectively, of the neck bridge of FIG. 13;

FIGS. 15A and 15B show a variation of the delivery shape and the unfolded configuration, respectively, of the neck bridge of FIG. 13;

DESCRIPTION OF THE PREFERRED EMBODIMENTS

The disclosed invention relates to devices and procedures for stabilizing the position and, in some instances, the structure of vaso-occlusive devices placed in a target occlusion site, usually an aneurysm. Use of the retaining devices and neck bridges disclosed herein reduce the potential migration of vaso-occlusive devices (e.g., helically wound coils) from target occlusion sites, by forming at least a partial barrier at the entrance zone to the aneurysm, i.e., where the aneurysm meets a feeding vessel.

Figure 1:
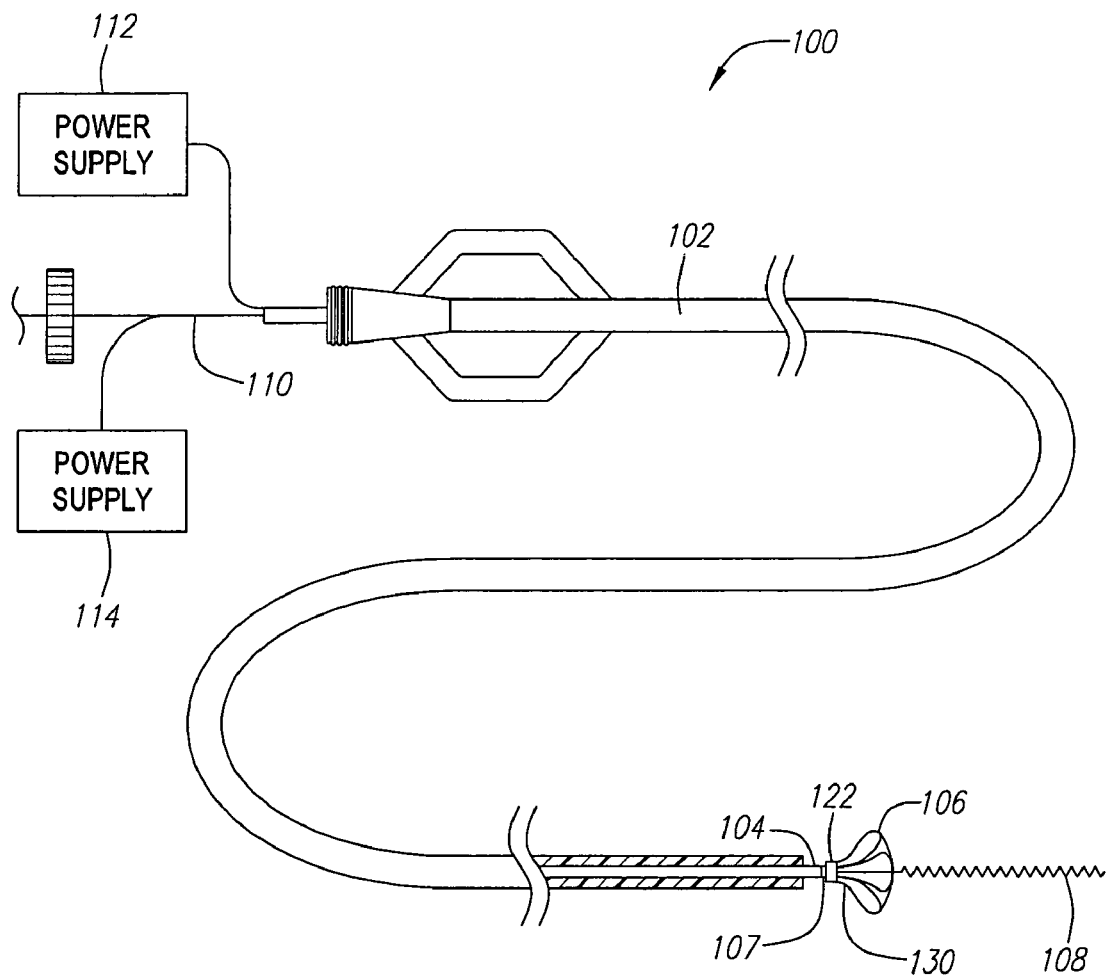
FIG. 1 is a cross sectional plan view of an aneurysm treatment system including a neck bridge comprising an array of elements in accordance with a preferred embodiment of the invention.

FIG. 1 shows an aneurysm treatment system 100, which includes an aneurysm neck bridge 106 constructed in accordance with a preferred embodiment. The aneurysm treatment system 100 also includes a tubular delivery catheter 102, and an inner elongated tubular member 104 slidable within the tubular delivery catheter 102. The aneurysm neck bridge 106 is removably coupled to a distal end 107 of the elongated tubular member 104 via an electrolytically severable joint 122, and is configured to be placed within an aneurysm sac or directly across a neck (i.e., in between the tissue defining the neck) of an aneurysm. The system 100 further includes a vaso-occlusive device 108 that is deliverable via the inner tubular member 104. The vaso-occlusive device 108 is coupled to a core wire 110 via another electrolytically severable joint 130. The severable joints 122 and 130 are of a scale that cannot easily be seen in FIG. 1 and are depicted in greater clarity in FIG. 2.

Schematically, the electrolytically severable joints 122 and 130 are configured to electrically couple to first and second power supplies 112 and 114, respectively, which are used to deliver current to sever the respective joints in a well known manner. The severance of the severable joints 122 and 130 releases the aneurysm neck bridge 106 and the vaso-occlusive device 108, respectively, at the site. Alternatively, a single power supply may be used to supply current for detachment of the vaso-occlusive device 108 and the aneurysm neck bridge 106.

Figure 2:
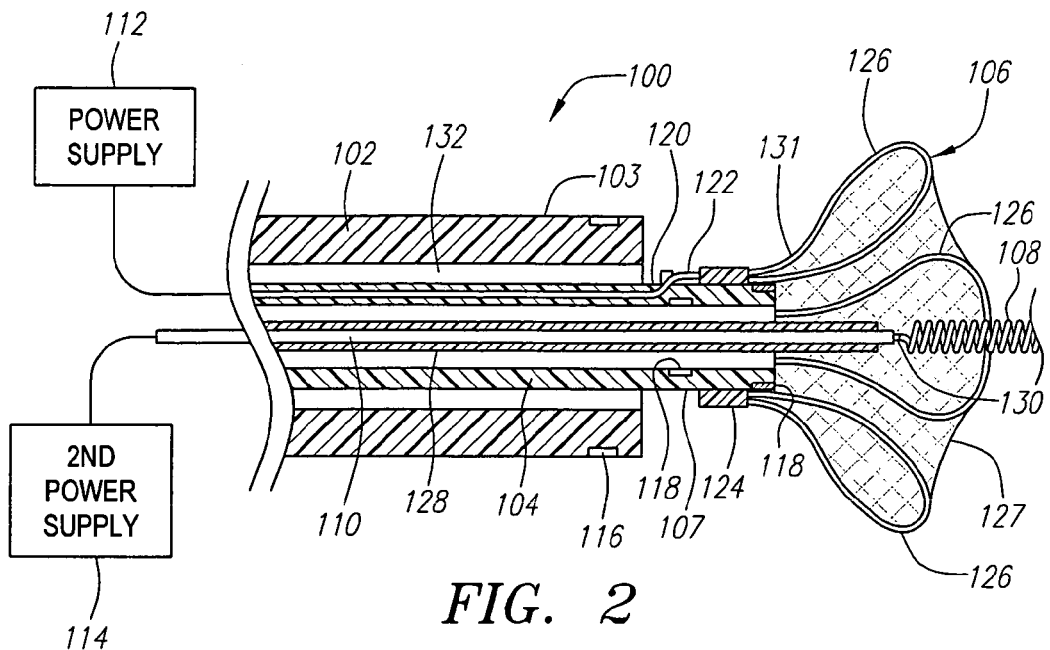
FIG. 2 is a partial cross sectional view of a distal end of the system of FIG. 1.

FIG. 2 is a partial cross section of a distal end of the system 100. The distal end 103 of delivery catheter 102 carries a radio-opaque marker 116 to assist navigating the distal end 103 through a vasculature. The inner tubular member 104 also carries a radio-opaque marker 118. In alternate embodiments, the inner tubular member 104 may have a shape other than that shown in FIG. 2. For example, the inner tubular member 104 may have an angle or a curvilinear shape. Preferably, the inner tubular member 104 is malleable or heat settable so that a physician or operator can create a desired shape at the time the system 100 is used.

A conductor wire 120 is provided for conducting current from the first power supply 112 to the electrolytically detachable joint 122. The aneurysm neck bridge 106 includes a junction region 124, which is detachably coupled to a distal end 107 of the inner delivery member 104. The junction region 124 may include an opening 128 (shown in FIG. 5), and may have a shape of a tubular member or a ring. The junction region 124 preferably fits around the inner tubular member 104 in a loose manner, and is maintained in position only by the electrolytic joint 122. In alternate embodiments, the exterior profile of the junction region 124 can vary from the circular shape shown in the illustrated embodiment. Examples of variations in the shape of the junction region 124 are shown and described herein.

The severable joint 122 is preferably created by insulating a portion of the conductor wire 120. For example, a portion of the conductor wire 120 may be insulated with an electrical insulator which is not susceptible to dissolution via electrolysis in blood or other ionic media, leaving the un-insulated portion of the conductor wire 120 susceptible to electrolytic dissolution. The electrical insulator may be the wall of the tubular member 104, as shown in FIG. 2, or alternatively, it may be a coating placed over the conductor wire 120. Suitable coatings include insulating materials, such as polyfluorocarbons (e.g., Teflon), polyurethane, polyethylene, polypropylene, polyimides, and other suitable polymeric materials. It will also be apparent that the sacrificial joint 122 is more susceptible to electrolysis than any other element of the device located near that joint 122. In use, current supplied by the first power supply 112 passes to the electrolytically severable joint 122, typically with the cooperation of an external return electrode pad (not shown) placed on a skin of a patient to complete the circuit. Passage of current through the electrolytically severable joint 122 causes the joint 122 to severe, thereby de-coupling the neck bridge 106 from the tubular member 104. Further information regarding the construction, placement, and other physical details of electrolytically severable joints used may be found in U.S. Pat. Nos. 5,234,437, 5,250,071, 5,261,916, 5,304,195, 5,312,415, and 5,350,397, the disclosures of which are expressly incorporated by reference herein. It will be appreciated that mechanical joints, and other types of detachable joints known in the art for placing occlusive devices in aneurysms may alternatively be used to couple the neck bridge 106 to the tubular member 104. Examples of such mechanical joints may be found in U.S. Pat. No. 5,234,437, to Sepetka, U.S. Pat. No. 5,250,071 to Palermo, U.S. Pat. No. 5,261,916, to Engelson, U.S. Pat. No. 5,304,195, to Twyford et al., U.S. Pat. No. 5,312,415, to Palermo, and U.S. Pat. No. 5,350,397, to Palermo et al, the disclosures of which are expressly incorporated herein by reference.

As shown in FIG. 2, because the neck bridge 106 is coupled to the tubular member 104 in a way that does not obstruct the distal opening 131 of the tubular member 104, the vaso-occlusive device 108 may be delivered via the inner tubular member 104. In the illustrated embodiment, the vaso-occlusive device 108 is detachably coupled to a distal end of the core wire 110 by the electrolytically severable joint 130, which is formed by insulating a proximal portion of the core wire 110 by an insulating layer 128. As noted above, delivery of vaso-occlusive devices using an electrolytically severable joint is well known in the art. Alternatively, the vaso-occlusive device 108 may be delivered by using a pusher or plunger, the distal advancement of which within the inner tubular member 104 pushes the vaso-occlusive device 108 out from the distal end of the inner tubular member 104. Other methods of delivering the vaso-occlusive device 108 known in the art may also be used.

Figure 3:
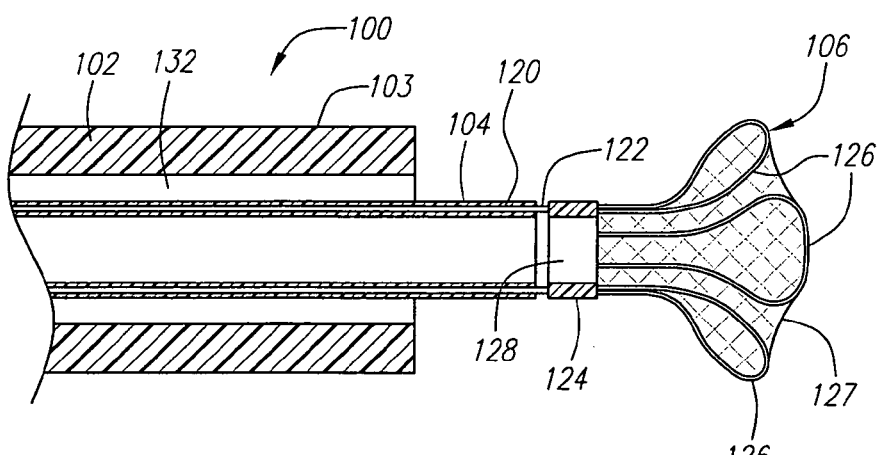
FIG. 3 is a partial cross sectional view of a variation of the distal end of the system of FIG. 1, particularly showing a junction region of the neck bridge coupling to a distal tip of an inner tubular member.
Figure 4:
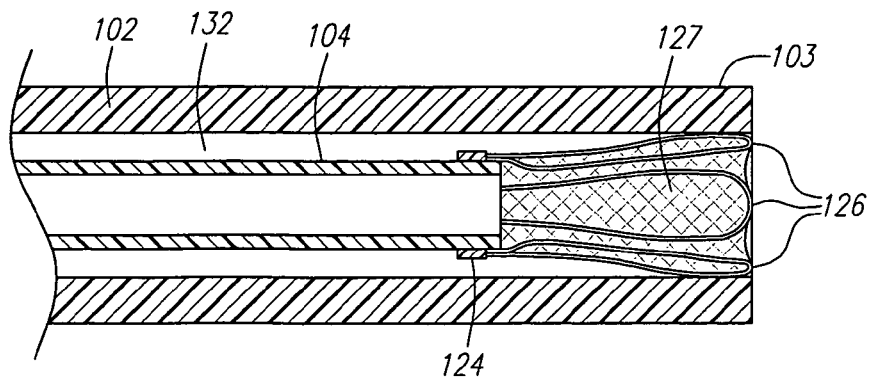
FIG. 4 is a partial cross sectional view of the distal end of the inner tubular member shown in FIG. 3, particularly showing the neck bridge assuming a delivery shape.

FIG. 3 shows another variation of the neck bridge 106. Unlike the previously shown embodiment, in which the junction region 124 of the neck bridge 106 is configured to fit around the distal end 107 of the inner tubular member 104, the junction region 124 of the neck bridge 106 of FIG. 4 is distal to the distal end 107 of the tubular member 104, and is configured to couple to a distal end 107 of the inner tubular member 104 via the severable joint 122. In this variation, the cross sectional dimension of the junction region 124 is substantially the same as the cross sectional dimension of the inner delivery member 104 to form a substantially continuous outer surface. Vaso-occlusive devices 108 exiting the distal end 107 of the tubular member 104 can be delivered to an aneurysm by passing through the opening 128 of the junction region 124, as discussed previously. The distal end 107 of the inner tubular member 104 may further include a Teflon liner or an extension (not shown) coupled to the interior surface of the inner tubular member 104, such that fluid (e.g., an embolic agent) can be delivered through the opening 128 of the junction region 124 without escaping into the gap between the tip of the inner tubular member 104 and the junction region 124.

The neck bridge 106 includes one or more radially expanding array elements or wires 126 attached to the junction region 124, and a cover 127 attached to the junction region 124. In alternate embodiments, the cover 127 may also be secured to the array elements 126. In further alternate embodiments, the cover 127 may be attached to both the array elements 126 and the junction region 124. Upon placement in an aneurysm, the array elements 126 together with the cover 127 spread to the general shape shown in FIG. 2. In the illustrated embodiment, each of the array elements 126 is a wire loop or ribbon rim. The number of array elements 126 may vary between embodiments, depending on factors such as the size of an aneurysm, the width of the tubular delivery catheter 102, and the thickness of the wire making up the array elements 126. Before the neck bridge 106 is deployed to a target site, the neck bridge 106 resides within a lumen 132 of the delivery catheter 102, and it is generally stretched to assume and maintain the shape of the lumen 132 as shown in FIG. 4. The cover 127 is folded into a low profile when positioned in the lumen 132. When the neck bridge 106 is pushed from the distal end of the delivery catheter 102, the array elements 126 assume their so-called "unfolded" shapes or configurations, thereby unfolding the cover 127.

The array elements 126 may be required to undertake relatively significant changes in shape during deployment of the neck bridge 106. To undertake such stress, it is usually preferable that the array elements 126 be produced of a material such as a super-elastic alloy. Super-elastic or pseudoelastic shape recovery alloys are well known in this art. For instance, U.S. Pat. Nos. 3,174,851; 3,351,463; and 3,753,700 each describe one of the more well known super-elastic alloys, known as Nitinol. These alloys are characterized by their ability to be transformed from an austenitic crystal structure to a stress-induced martensitic (SIM) structure at certain temperatures and then to return elastically to the austenitic shape when the stress is removed. These alternating crystal structures provide the alloy with its super-elastic properties.

The above described alloys are especially suitable because of their capacity to recover elastically, and almost completely to an unfolded configuration once a bending stress is removed. Typically during use, these alloys suffer little permanent plastic deformation, even at relatively high strains. This ability allows the neck bridge 106 to undertake substantial bends while residing within the lumen 132 of the tubular delivery catheter 102 and while passing through a vasculature. In spite of this bending, the neck bridge 106 returns to its original shape, i.e., unfolded configuration, without retaining any substantial permanent kinks or bends once deployed from the lumen 132.

Of the super-elastic alloys currently available, the preferred material is 50.6.+−0.2% nickel with most of the remainder being titanium. Up to about 5% of the alloy may be a member of the iron group of metals, particularly chromium and iron. The alloy is preferred to not contain more than about 500 parts per million of oxygen, carbon, or nitrogen. The transition temperature of this material is not particularly important, but it should be reasonably below the typical temperature of the human body so as to allow it to be in its austenitic phase during use. The wires or ribbons making up the various array elements 126 preferably have a diameter less than about 0.010 inches. These super-elastic alloys are not always sufficiently visible under fluoroscopy as it is used in the human body. Consequently it may be desirable to add a radio-opacity covering to the array elements 126. Radio-opaque metals such as gold and platinum are well known. Radio-opaque metals may be added to the array elements 126 by plating or by wrapping the array element 126 in a radio-opaque wire or ribbon, as is known in the art. Alternatively, one or more radio-opaque markers may be secured to the array elements 126, for example at a perimeter of the neck bridge defined by the array elements 126.

Other metals may also be appropriate for construction of the array elements 126. Such metals include stainless steels and other highly elastic, if not super-elastic, alloys. Polymeric materials which are somewhat easier to work with in forming a device may also be used for construction of the array elements 126. Polymeric materials are somewhat easier to work with in forming a device. Such polymeric materials may include members from the group of polyethylene, polypropylene, polytetraflouroethylene, various Nylons, and the like. Suitable polymers may also include most biocompatible materials, which may be made into fibers, including thermoplastics, e.g., polyesters such as polyethyleneterephthalate (PET) especially Dacron; polyamides including Nylons; polyolefins such as polyethylene, polypropylene, polybuylene, their mixtures, alloys, block and random copolymers; polyglycolic acid; polylactic acid; fluoropolymers (polytetrafluoro-ethylene), or even silk or collagen.

FIG. 5 shows a top view of the neck bridge 106. As shown in FIG. 5, the cover 127 is unfolded to have a substantially continuous surface when the array elements 126 assume their unfolded configurations. The cover 127 may be a fabric, a woven or non-woven mesh, or other sheeting or planar structure. Although the array elements 126 are each preferably of a form that retains a large measure of elasticity after having been bent, the cover 127 may be less elastic. The cover 127 may be made from a variety of materials such as polymers, nylons, and polyester. These materials do not provide substantial strength to the cover 127, so as to allow the device to be readily folded into a low profile and placed into the delivery catheter lumen 132 without adding unnecessary stiffness. The sole function of the cover 127 is to remain an implanted vaso-occlusive device in an aneurysm. The function of the array elements 126 is to maintain the structural integrity of the neck bridge device as it is situated within an aneurysm. Alternatively, the cover 127 may be made to have a similar elasticity as the array elements 126. Therefore, any of the materials discussed previously with reference to the array elements 126 may also be suitable for construction of the cover 127. Other materials suitable for construction of the cover 127 include Dacron (polyethyleneterephthalate), collageneous materials, polyluorocarbons, combinations thereof, and other vascular graft materials. Fibrous materials, such as polyglycolic acid, wool, or cotton, may also be used.

FIG. 6 shows a variation of the cover 127, which has a braided or mesh-like structure. In the illustrated embodiment, the neck bridge 106 includes six array elements 126 attached to the cover 127. The cover 127 includes a plurality of loops 210, each of which formed by securing ends of a fiber to the junction region 124. The loops 210 may overlap one another, or alternatively, be inter-woven with each other, to form the cover 127. It should be noted that the shape of the loop 210 is not limited to that shown in the illustrated embodiment. Furthermore, the cover 127 may have different braided patterns than those shown herein.

In each of the above-described embodiments of the neck bridge, the cover 127 may be placed at a top side of the array elements 126 (FIG. 7A), a bottom side of the array elements 126 (FIG. 7B), or it may cover both sides of the array elements 126 (FIG. 7C). In the embodiment shown in FIG. 7C, the neck bridge may further include a disk (not shown) placed between the bottom and top surfaces of the cover 127 for reducing the porosity of the neck bridge.

Notably, the shape of the cover 127 is not limited to the circular shape shown in the previously discussed embodiments. The cover 127 can have other shapes, such as an elliptical or rectangular shape (FIG. 8).

Generally, as with the embodiments shown in FIGS. 7A and 7C, the cover 127 is not required to be directly secured to any of the array elements 126. Rather, the array elements 126 exert a bearing and/or frictional force on the cover 127 when they assume an unfolded configuration. However, the cover 127 may optionally be secured to the array elements 126 at one or more various points. The securing may be accomplished using a glue, epoxy, heat bond, or other suitable adhesives, depending upon the materials from which the respective cover 127 and array elements 126 are made. By way of further example, the cover 127 may also be secured to the array elements 126 by sewing them together using a thread. Securing the cover 127 to the array elements 126 may assist the array elements 126 in unfolding the cover 127 into a desired shape as the array elements 126 assume their unfolded configurations. Alternatively, the array elements 126 may be embedded within the cover 127, or inter-woven with the cover 127.

It should be noted that the shape of the individual array element is not limited to the loop shape shown in the previous embodiments, and that the array element 126 may have other shapes as well. FIG. 8 shows a variation of the array element 126 that has a substantially rectilinear profile. As shown in the illustrated embodiment, the array elements may optionally have blunted tips to avoid trauma to the arteries in which they are placed. The array elements 126 may also have other shapes as well. In the embodiment of FIG. 8, the cover 127 has a rectangular shape, as previously noted.

Figure 9B:
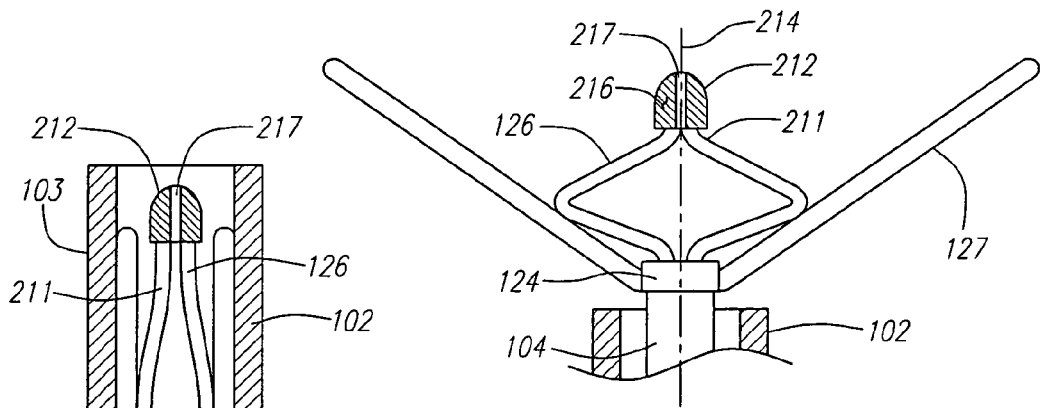
FIGS. 9A and 9B show another variation of the neck bridge, particularly showing the array elements having different unfolded configurations.
Figure 9A:

The manner in which the array elements fold or bend when positioned within the lumen of a tubular delivery member is not limited. By way of illustration, FIGS. 9A and 9B show another variation of the neck bridge, wherein the array elements 126 are folded in a manner that is different from that shown in FIG. 4. In the embodiment of FIGS. 9A and 9B, each of the array elements 126 has an end 211 coupled to a tip 212. The tip 212 includes a radio-opaque marker 216. The tip 212 also includes an opening 217 through which a vaso-occlusive device or occlusion fluid may be delivered. The array element 126 has a mid portion that flares outward while maintaining the end 211 of the array element 126 in close proximity to an axis 214 of the junction region 124. The array elements 126 are stretched to the delivery shapes shown in FIG. 9A when positioned within the lumen 132 of the delivery catheter 102, and assume the unfolded configurations shown in FIG. 9B when unconfined outside the delivery catheter 102. The array elements 126 can also have curvilinear shapes or other unfolded configurations, so long as the array elements 126 unfold the cover 127 once deployed outside the lumen 132 of the delivery catheter 102.

Figure 10A:
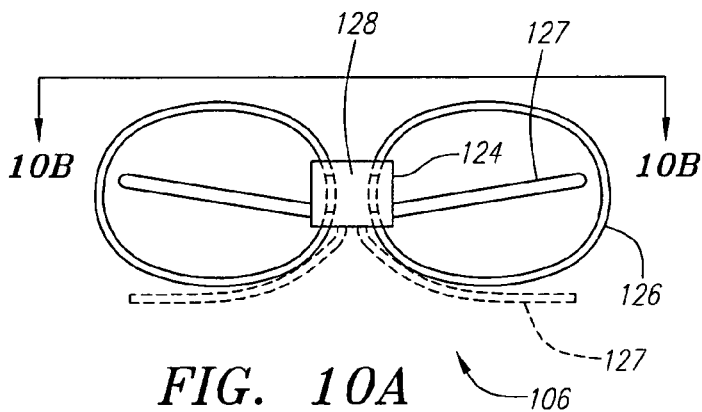
FIGS. 10A and 10B show yet another variation of the neck bridge, particularly showing the array elements having upright loop shapes.
Figure 10B:
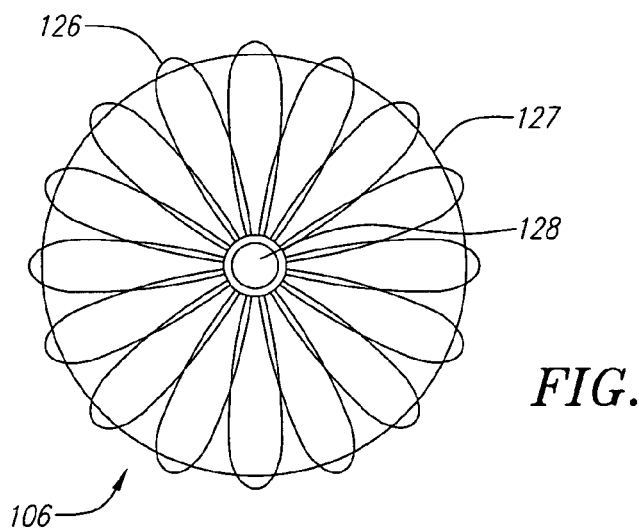

FIGS. 10A and 10B, respectively show side and top views of another variation of the neck bridge 106, wherein the array elements 126 have upright loop shapes. Although the array elements 126 are shown attaching to an interior surface of the junction joint 124, the array elements 126 may also be secured to the ends or the side of the junction joint 124. In the illustrated embodiment, the array elements 126 wrap around a perimeter of the cover 127 such that the cover 127 is between the ends of the wires defining the loop shape array elements 126. Alternatively, as shown by the dashed-lines, the cover 127 may also be placed at a bottom side of the array elements 126.

Figure 11:
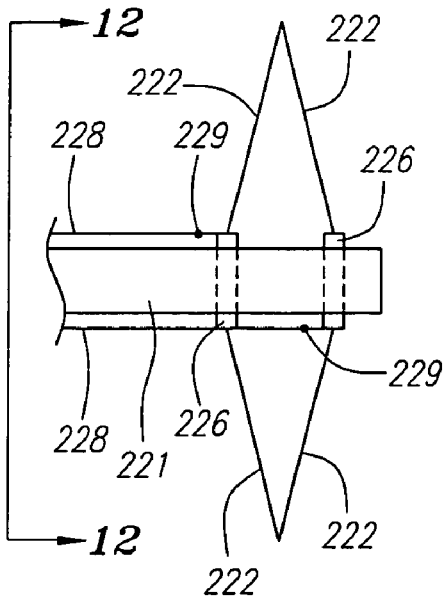
FIG. 11 is a side view of a still another variation of the neck bridge, particularly showing the neck bridge having a pair of collars coupled to control wires.
Figure 12:
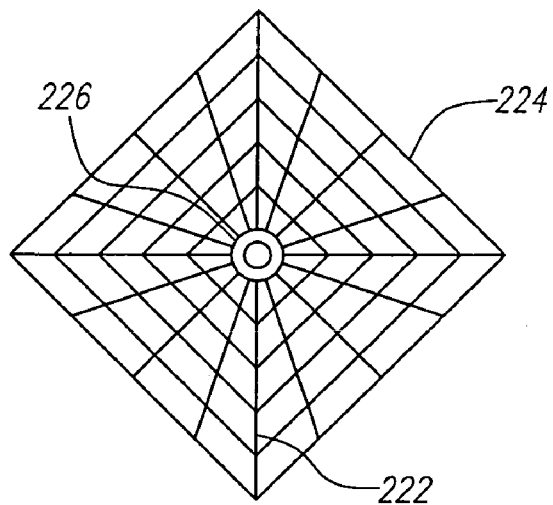
FIG. 12 is a top view of the neck bridge of FIG. 11 in a deployed (i.e., non-constrained) configuration.

The array elements 126 may also be deployed using mechanical methods. FIG. 11 shows another variation of the neck bridge 220 that is delivered on the exterior of a delivery member 221. This variation includes a number of radially extending array elements 222 which are joined at their outer ends. The radially extending array elements 222 are joined by a cover 224 which also may be scrim-like. The array elements 222 are joined to a pair of collars 226 that slide on the delivery member 221 and are controlled by one or more control wires 228. Each of the control wires 228 may have a releasable joint 229, desirably an electrolytically severable joint, as discussed previously. During delivery of the neck bridge 220, the array elements 222 lie generally against the delivery member 221. During deployment, the control wires 228 are axially manipulated to extend the radially extending array elements 222 into the deployed shape depicted in FIG. 12.

Figure 13:
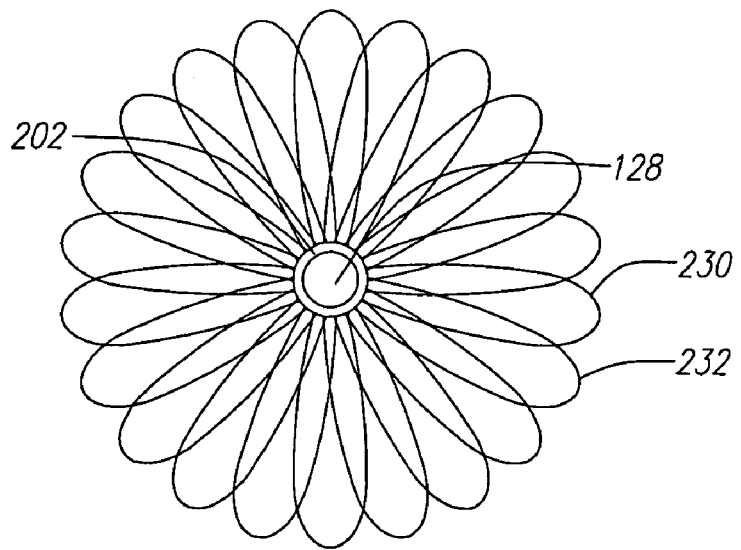
FIG. 13 is a top view of yet another variation of the neck bridge, particularly showing the neck bridge having a braided structure.

In the previously discussed embodiments, the neck bridge includes one or more array elements attached to the cover. However, the array elements may not be required. FIG. 13 shows a variation of the neck bridge which includes a junction region 202 and a braided or mesh-like structure 230 secured to the junction region 202. The braided structure 230 may carry a radio-opaque marker (not shown), or be plated or coated with a radio-opaque material. The braided structure 230 is preferably made from an elastic material, such as Nitinol. However, any of the materials discussed previously with reference to the array element 216 may also be suitable for construction of the braided structure 230. The advantage of making the braided structure 230 using elastic material is that the braided structure 230 can assume an unfolded shape without the help of the array elements. The braided structure 230 may also be made from a radio-opaque material. In the illustrated embodiment, the braided structure 230 includes a number of loops 232, each of which formed by securing ends of a fiber to the junction region 202. However, the braided structure 230 can have other woven or non-woven patterns as well. FIGS. 14A and 14B show that the braided structure 230 can assume a delivery shape by bending the loops 232 such that the portions of the loops 232 defining the periphery of the braided structure 230 are distal to both ends of the fibers making up the loops 232.

FIGS. 15A and 15B show a variation of the neck bridge of FIG. 13. As shown in the embodiment, a first end of the fiber making up each of the loops 232 is secured to a first portion 202a of the junction region 202, and a second end of the fiber making up each of the loops 232 is secured to a second portion 202b of the junction region 202. When residing within the delivery catheter 102, the braided structure 230 is stretched or bent into a delivery shape such as that shown in FIG. 15A. When the neck bridge is deployed outside the delivery catheter 102, the first portion 202a and the second portion 202b of the junction region move closer to each other, and the portion of the loop 232 near the mid-section 234 of the loop 232 becomes the periphery of the braided structure 230. It should be noted that the manner in which the braided structure 230 is folded or deployed should not be limited to the examples described previously, and that other methods of folding or deploying the braided structure 230 can also be used.

Figure 16:
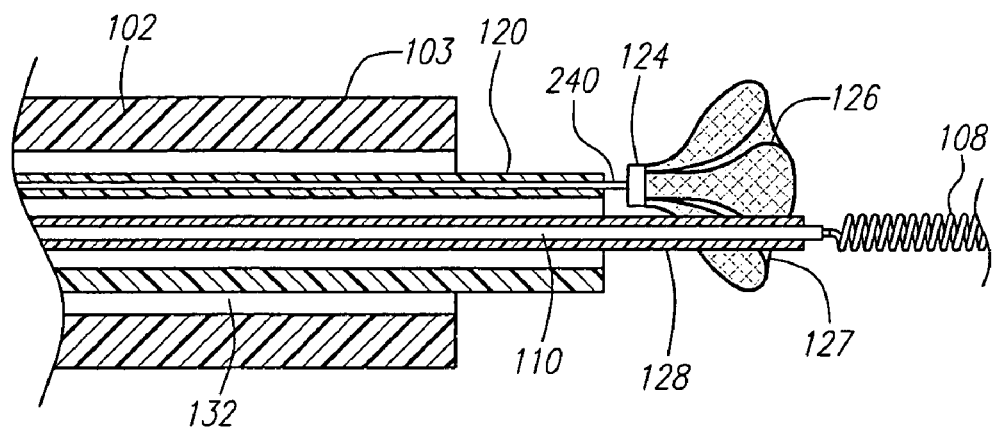
FIG. 16 is a further variation of the neck bridge, particularly showing the junction region of the neck bridge coupled to a wall section of the inner tubular member.

In all of the previously described embodiments, the junction region includes the opening 128 through which a vaso-occlusive device 108 may be delivered. However, the opening 128 is optional. FIG. 16 shows a cross sectional view of a variation of the junction region 124 that does not have the opening 128. In the illustrated embodiment, the junction region 124 is detachably secured to a wall section of the inner tubular member 104 by an electrolytically severable joint 240. The vaso-occlusive device 108 may also be delivered via the inner tubular member 104, as discussed previously.

Figure 17:
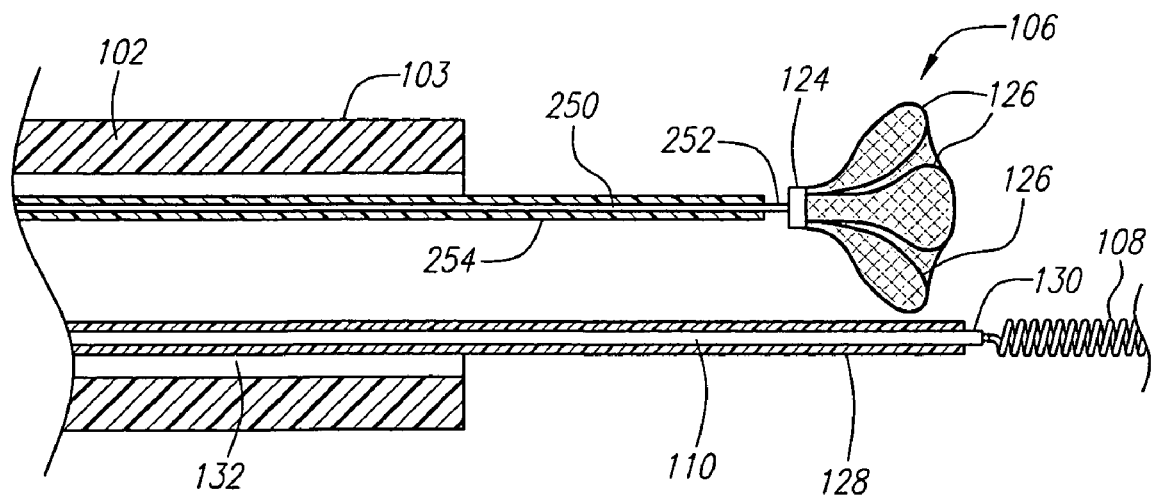
FIG. 17 is a still further variation of the neck bridge, particularly showing the junction region of the neck bridge coupled to a core wire by a severable joint.

The neck bridge 126 may be detachably coupled to other structures instead of the inner tubular member 104 described previously. FIG. 17 shows a cross sectional view of a neck bridge 126 that is detachably coupled to a core wire 250 by an electrolytically severable joint 252. A proximal portion of the core wire 250 is insulated by an insulating layer 254 to form the severable joint 252. In this case, the delivery catheter 102 is used to deliver both the neck bridge 106 and the vaso-occlusive device 108.

The method of using the previously described neck bridges will now be discussed with reference to FIGS. 18A-18E. First, the delivery catheter 102 is inserted into the body of a patient. Typically, this would be through a femoral artery in the groin. Other entry sites sometimes chosen are found in the neck and are in general well known by physicians who practice these types of medical procedures. The delivery catheter 102, which may be a microcatheter or a sheath, may be positioned so that the distal end of the delivery catheter 102 is appropriately situated, e.g., near the neck of an aneurysm 306 to be treated. (FIG. 18A) The placement of the delivery catheter 102 may be assisted by the use of guide wire and/or a radio-opaque marker, as are known in the art.

Figure 18A:
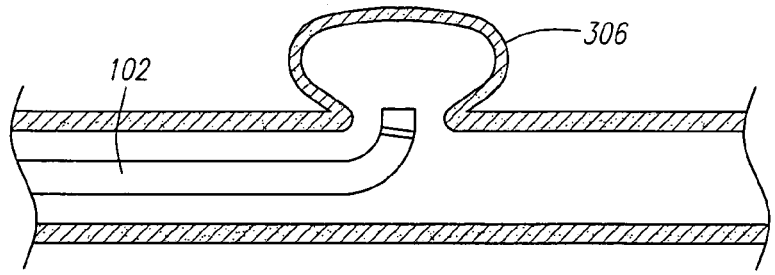
FIGS. 18A-18E show a procedure for introducing an embodiment of the neck bridge, along with a vaso-occlusive device, into an aneurysm.
Figure 18B:
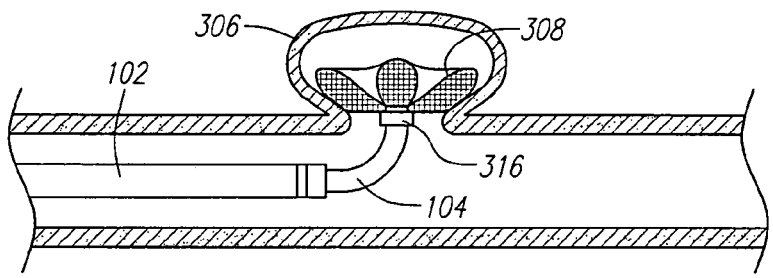
Figure 18C:
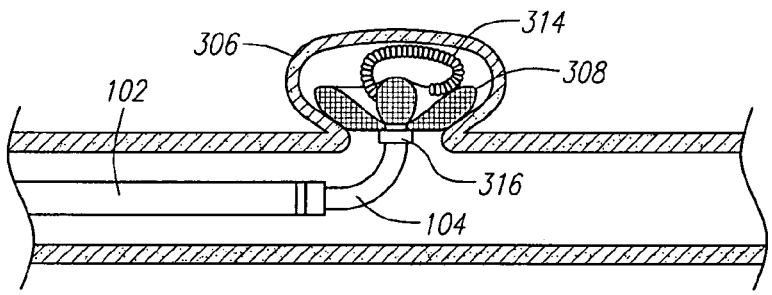
Figure 18D:
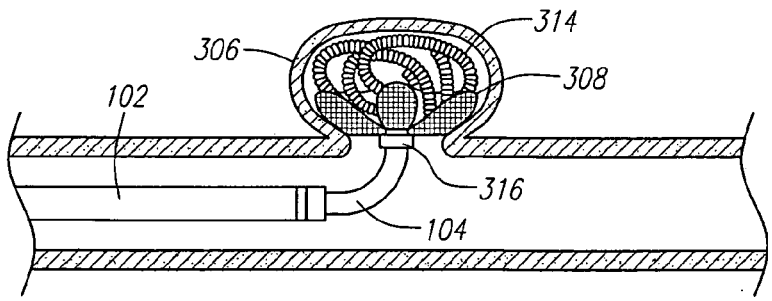

A neck bridge 308, which is representative of any of the embodiments of the neck bridge discussed previously, is carried within the delivery catheter 102 before it is deployed. While positioned within the delivery catheter 102, the neck bridge 308 is stretched into a delivery shape. If the neck bridge 308 is coupled to the inner tubular member 104, the neck bridge 308 may be deployed by retracting the delivery catheter 102 relative to the tubular member 104, or by advancing the tubular member 104 relative to the delivery catheter 102. Alternatively, if the neck bridge 308 is coupled to the core wire 250, such as that shown in FIG. 17, the neck bridge 308 may be deployed by retracting the delivery catheter 102 relative to the core wire 250 or by advancing the core wire 250 relative to the delivery catheter 102. Once the neck bridge 308 is unconfined outside the delivery catheter 102, it assumes an unfolded configuration. FIG. 18B shows the neck bridge 308 having been deployed and placed within the aneurysm 306.

Next, one or more vaso-occlusive devices 314 may be delivered into the aneurysm using any of the conventional methods. (FIG. 18C) If the neck bridge 308 includes a junction region 316 that has an opening, such as the opening 128 shown in FIG. 5, the vaso-occlusive device 314 may be delivered via the inner tubular member 104, through the opening 128 of the junction region 316 of the neck bridge 308, and into the aneurysm 306. It should be noted that instead of vaso-occlusive devices, other occlusion substance such as occlusion fluid or occlusion particles may also be delivered through the opening of the junction region 316 and into the aneurysm 306. If the junction region 316 of the neck bridge 308 does not have an opening, such as the embodiment shown in FIG. 16 or 17, the vaso-occlusive device 314 may be delivered to the aneurysm 306 along a path that is exterior to the tubular member 104 or to the core wire 250 if one is used. In this case, the neck bridge 308 should be made sufficiently flexible to distend around the vaso-occlusive delivery device. Alternatively, the vaso-occlusive device 314 may be delivered into the aneurysm 306 by going through an opening in the cover, such as a pre-made opening, or an opening defined by the fibers making up the cover. The vaso-occlusive device 314 may also be delivered into the aneurysm by puncturing the cover of the neck bridge 308.

Figure 18E:
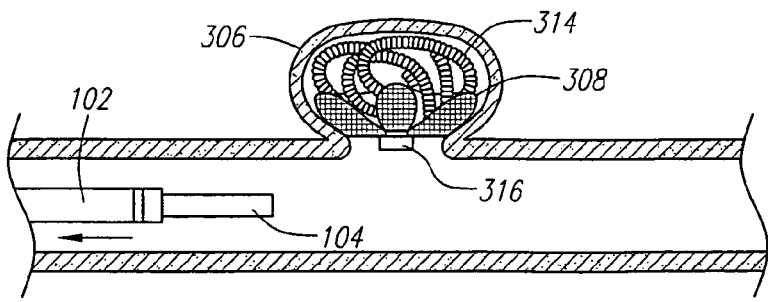

After a desired number of the vaso-occlusive coils 314 have been placed in the aneurysm 306, the electrolytically severable joint 122 (or joint 129, 140, or 252) is then severed, thereby de-coupling the neck bridge 308 from the tubular member 104 or from the core wire 250 if one is used. (FIGS. 18D and 18E) The delivery catheter 102 and the inner tubular member 104 are then withdrawn, leaving the vaso-occlusive device 314 in place within the aneurysm 306. As shown in FIG. 18E, the neck bridge 308 stabilizes the presence of the vaso-occlusive device 314 and prevents the vaso-occlusive coil 314 from being drawn or escaping into the feed vessel. If desired, a stent or a perfusion balloon may optionally be placed in the parent vessel to help seat the neck bridge 308 within the aneurysm 306.

Figure 19A:
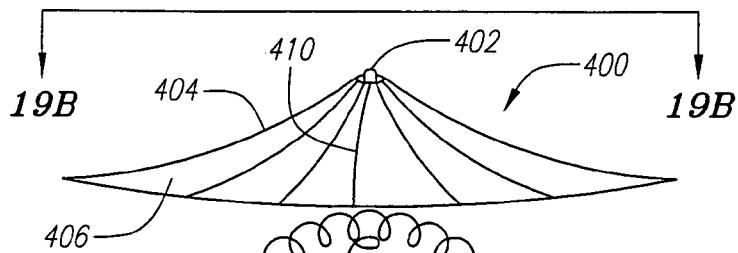
FIG. 19A shows a side view of an embodiment of a neck bridge in combination with an "anchor" adapted to be placed within an aneurysm.
Figure 19B:
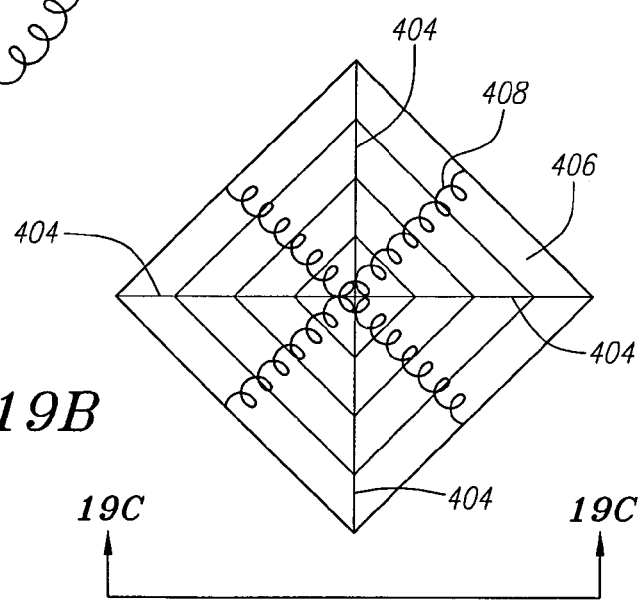
FIG. 19B is a top view of the neck bridge of FIG. 19A.
Figure 19C:
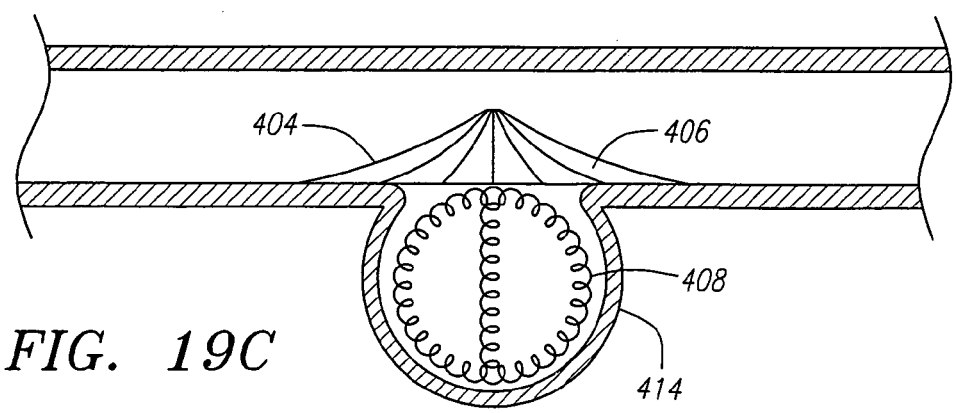
FIG. 19C shows a placement of the neck bridge depicted in FIG. 19A within an aneurysm.

It should be noted that the neck bridge may also be placed outside the neck of an aneurysm. FIGS. 19A-19C show another variation of the neck bridge 400 having a junction region 402, a number of radially extending array elements 404, and a cover 406. Unlike the previously described embodiments, the neck bridge 400 also includes a cage 408 made up of a plurality of, e.g., platinum or nickel-titanium coils or wires 409. A connector 410 connects the cage 408 to the junction region 402 or to the array elements 404, and is situated within the neck of the aneurysm after implantation. The array elements 404 are typically joined to a releasable joint, which may be an electrolytically severable joint as discussed previously. As may be seen from FIG. 19B, the cage 408 extends outwardly from the general center-line of the device and generally should be sized to conform to the size of, and generally to the shape of, the aneurysm. FIG. 19C shows the general placement of the device within an aneurysm 414. The cage 408, which is within the sac of the aneurysm 414, anchors the cover 406, which is placed outside the neck of the aneurysm 414. The method of using the neck bridge 400 is similar to that described previously with reference to FIGS. 18A-18E.

Many alterations and modifications may be made by those of ordinary skill in this art, without departing from the spirit and scope of this invention. The illustrated embodiments have been shown only for purposes of clarity and the examples should not be taken as limiting the invention as defined in the following claims, which are intended to include all equivalents, whether now or later devised.

What is claimed is:

1. A device for bridging a neck of an aneurysm, comprising:
   an elongate tubular member;
   a neck bridge comprising:
      a junction region operatively coupled to the elongate tubular member via an electrolytically severable joint;
      one or more radially extending array elements secured to the junction region, each array element having an unfolded shape and a delivery shape; and
      a cover attached to the junction region, an array element, or both, wherein the cover extends over the delivery shape of one of the array elements, wherein the neck bridge is configured for placement within or across the neck of the aneurysm.

2. The device of claim 1, wherein the junction region comprises a tubular section.

3. The device of claim 1, wherein each array element comprises a wire having a curvilinear shape.

4. The device of claim 1, further comprising a tip, wherein an array element comprises a wire having a first end attached to the tip and a second end attached to the junction region.

5. The device of claim 4, the tip having an opening through which a vaso-occlusive device or occlusion fluid may be delivered.

6. The device of claim 1, further comprising a radio-opaque marker carried on an array element.

7. The device of claim 6, wherein the radio-opaque marker is carried at a perimeter of the device.

8. The device of claim 1, wherein the array elements each comprises a resilient, substantially elastic material.

9. The device of claim 1, wherein the cover comprises polymer.

10. The device of claim 1, wherein the cover comprises polyester.

11. The device of claim 1, wherein the elongate member comprises a core wire.

12. The device of claim 1, wherein the elongate member comprises a radio-opaque marker at its distal end.

13. The device of claim 1, wherein the cover is attached only to one or more of the array elements.

14. The device of claim 1, wherein each array element comprises a wire loop.

15. The device of claim 14, each array element having first and second ends attached to the junction region.

16. The device of claim 1, wherein the cover is attached to the array elements by an adhesive.

17. The device of claim 1, wherein the array elements are inter-woven with the cover.

18. The device of claim 1, wherein the cover has a top side and a bottom side, and wherein the array elements are positioned between the top side and the bottom side of the cover.

19. The device of claim 1, wherein the cover is attached only to the junction.

* * * * *